(12) United States Patent
Park et al.

(10) Patent No.: US 9,474,816 B2
(45) Date of Patent: Oct. 25, 2016

(54) METHODS FOR DISPERSING DECONTAMINATION PRODUCTS

(71) Applicant: The Boeing Company, Seal Beach, CA (US)

(72) Inventors: Shawn Hyunsoo Park, Cerritos, CA (US); James J. Sheahan, Jr., Alton, IL (US); Charles E. Morris, Des Peres, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/218,054

(22) Filed: Mar. 18, 2014

(65) Prior Publication Data

US 2014/0205502 A1 Jul. 24, 2014

Related U.S. Application Data

(62) Division of application No. 12/685,355, filed on Jan. 11, 2010, now Pat. No. 8,715,586.

(51) Int. Cl.
*A61L 2/20* (2006.01)
*A61L 2/22* (2006.01)
*B05B 5/03* (2006.01)
*B05B 5/16* (2006.01)

(52) U.S. Cl.
CPC . *A61L 2/22* (2013.01); *B05B 5/03* (2013.01); *B05B 5/1608* (2013.01); *A61L 2202/15* (2013.01); *A61L 2202/16* (2013.01); *A61L 2202/25* (2013.01)

(58) Field of Classification Search
CPC .................................. A61L 2/22; B05B 5/03
USPC ........................................................ 422/33
See application file for complete search history.

(56) References Cited

U.S. PATENT DOCUMENTS

| 5,564,628 | A | 10/1996 | Hall et al. |
| 6,279,589 | B1 | 8/2001 | Goodley |
| 6,455,017 | B1 * | 9/2002 | Kasting et al. ............... 422/292 |

(Continued)

FOREIGN PATENT DOCUMENTS

| CN | 2834546 Y | 11/2006 |
| WO | 2009046563 A2 | 4/2009 |

OTHER PUBLICATIONS

Owners Manual ESS SC-EB: May 4, 2009; pp. 1-30.*

(Continued)

*Primary Examiner* — Kevin Joyner
(74) *Attorney, Agent, or Firm* — Armstrong Teasdale LLP

(57) ABSTRACT

An electrostatic spraying system for decontamination of a vehicle is described. The system includes a wheeled platform sized to fit inside the vehicle, at least one tank operable to contain one or more decontaminant agents, the tanks supported by said wheeled platform, a plurality of nozzles affixed to the wheeled platform, wherein each nozzle is positioned for distribution of the decontaminant agents in at least one pre-determined direction, an electrostatic charging system connected to each of the nozzles for applying an electrostatic charge to the decontaminant agents as the agents are dispersed, and at least one compressor in communication with the tanks for pressurizing the decontaminant agents. The one or more compressors are capable of providing a pressure sufficient to provide a constant distribution of the decontaminant agents through the electrostatic nozzles.

9 Claims, 6 Drawing Sheets

(56) References Cited

U.S. PATENT DOCUMENTS

| | | | |
|---|---|---|---|
| 8,287,816 B2* | 10/2012 | Kral | 422/300 |
| 2005/0074359 A1 | 4/2005 | Krieger et al. | |
| 2008/0063561 A1 | 3/2008 | Van Hooser | |
| 2008/0276408 A1 | 11/2008 | Gilbert, Jr. et al. | |

OTHER PUBLICATIONS

International Search Report and Written Opinion of PCT/US2010/059079; Nov. 15, 2011; 11 pages.

Hilsen, B.; Electrostatic Sprayers Now Being Used for Disinfecting and Deodorizing Facilities; http://www.free-press-release.com/new/print-1213109936.html; Jun. 10, 2008; 2 pages.

Electrostatic Spraying Systems, Inc.; http://www.maxcharge.com; 2009; 2 pages.

Sprayers for Electrostatic Spraying Systems, Inc.; http://www.prevent-staph.com/sprayers.html; 4 pages; date unknown.

China First Office Action for related application No. 201080061172.X dated Dec. 10, 2013.

Canada Office Action for related application 2,786,841 dated Oct. 14, 2015; 4 pp.

* cited by examiner

METHODS FOR DISPERSING DECONTAMINATION PRODUCTS

CROSS REFERENCE TO RELATED APPLICATIONS

This application is a divisional and claims priority to U.S. patent application Ser. No. 12/685,355, now U.S. Pat. No. 8,715,586, filed Jan. 11, 2010 for "METHODS AND SYSTEMS FOR DISPERSING DECONTAMINATION PRODUCTS", which is hereby incorporated by reference in its entirety.

BACKGROUND

The field of the disclosure relates generally to decontamination of enclosed spaces where persons periodically gather, and more specifically, to methods and systems for dispersing decontamination products such as biological and chemical decontamination products.

Recently, the Severe Acute Respiratory Syndrome (SARS) pandemic has revealed a clear vulnerability regarding global disease transmission, and its effect on the global economy. One industry that was seriously affected is the transportation industry which includes the airline industry. Current concerns over the H1N1 virus have reaffirmed the effect of such pandemics on the global economy as well as the economics of the airline industry. For example, during the SARS pandemic, airlines lost billions of dollars of revenue due to maintenance and reduced aircraft availability.

The long decontamination processes, currently recommended by the CDC requires using manual wipe out of the surfaces, which can be easily seen as impacting aircraft operation and could contribute to a loss of revenues for airlines. For example, manual disinfecting of an aircraft vehicle is very time consuming. For a typical commercial aircraft this manual wipe down process can take days or even weeks to complete. As the process is performed by airline personnel, there are limitations to this "cloth and bucket" approach. Manual sprayers are known, but again, such a process can be inadequate and less efficient.

BRIEF DESCRIPTION

In one aspect, a method for dispersing a decontamination agent within a vehicle cabin is provided. The method includes dispersing electrostatically charged decontamination agent from a tank positioned within a rolling cart to one or more defined areas within the vehicle cabin, positioning a plurality of automatic electrostatic nozzles for distribution of the decontamination agent in at least one predetermined direction, wherein the plurality of automatic electrostatic nozzles are configured to move in one or more dimensions to be selectively stowable within the rolling cart as the plurality of automatic electrostatic nozzles remain attached to the rolling cart. The method also includes applying an electrostatic charge to the decontamination agent with an electrostatic charging system connected to at least one of the plurality of automatic electrostatic nozzles, wherein the electrostatic charge is applied as the decontamination agent is dispersed, and pressurizing the decontamination agent with at least one compressor in communication with the tank. The at least one compressor is capable of providing a pressure sufficient to provide a substantially constant distribution of the decontamination agent through at least one of the plurality of automatic electrostatic nozzles.

The features, functions, and advantages that have been discussed can be achieved independently in various embodiments of the present invention or may be combined in yet other embodiments further details of which can be seen with reference to the following description and drawings.

DETAILED DESCRIPTION

As further disclosed by the described embodiments, a self contained system is described for air and ground transport vehicle systems, as well as permanently placed ground structures. The system provides a mechanism enabling the interior decontamination of such structures against influenza viruses, bacteria, chemical agents, and biological agents, to name a few. Embodiments of the device include a manually operated hand sprayer which is used for localized dispersion, and a plurality of automatically operated spray nozzles, mounted such that they will disperse decontaminants via electrostatic spray, for example, to assure complete coverage of the vehicle interior, resulting in decontamination with minimal maintenance. In one preferred embodiment, the use of electrostatic spray results in two micron to forty micron size droplets, which allows for the use of less decontamination agent than at least certain current decontamination methods and also minimizing material damages due to contact with decontaminant agents.

In one embodiment, the disclosed system is an integrated system that can be housing in a device similar to an existing aircraft service/food cart, which allows for storage within the aircraft (replacing one of the service/food carts). In one scenario, such a system would replace one of the service/food carts during a pandemic. Such a system would then be periodically guided down one or more aisles of an aircraft, manually or automatically, while manually and/or automatically dispersing one or more decontamination agents. While described in terms of a commercial aircraft implementation, other aircraft (military, private, cargo) applications are also contemplated as well as applications within ground transport vehicles and buildings. As further described within, the system is operable for the optional manual spraying of localized areas with a variety of chemical and biological decontamination agents, and further operable for the automatic spraying of the remaining areas of the aircraft, for example, using electrostatic spray nozzles for aircraft interior decontamination using such chemical, biological, and/or other decontamination agents.

Figure 1:
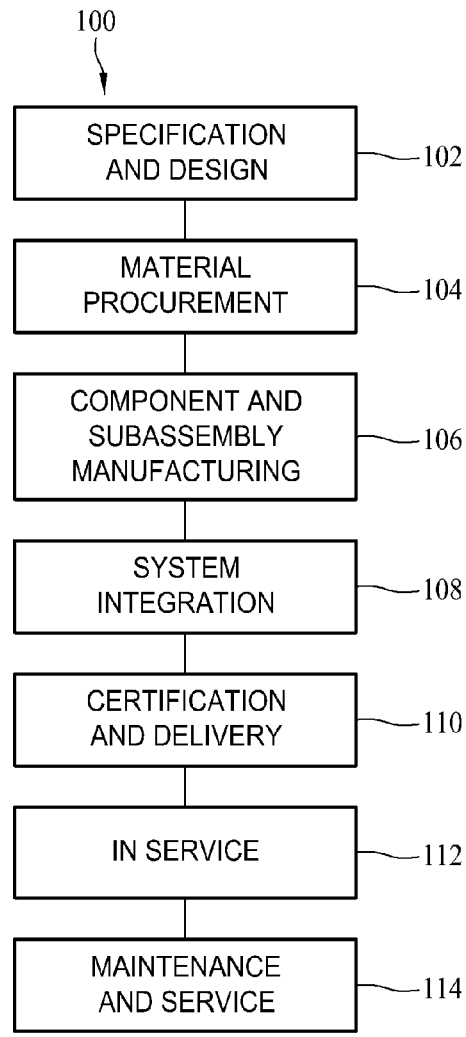
FIG. 1 is a flow diagram of an aircraft production and service methodology.
Figure 2:
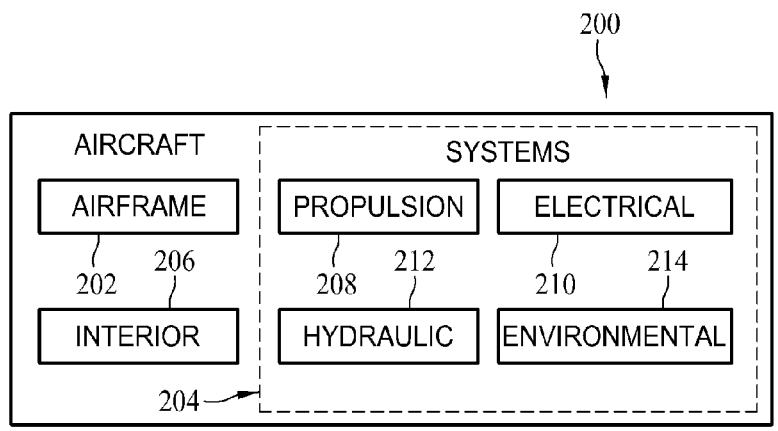
FIG. 2 is a block diagram of an aircraft.

Referring more particularly to the drawings, embodiments of the disclosure may be described in the context of aircraft manufacturing and service method 100 as shown in FIG. 1 and an aircraft 200 as shown in FIG. 2. During pre-production, aircraft manufacturing and service method 100 may include specification and design 102 of aircraft 200 and material procurement 104.

During production, component and subassembly manufacturing 106 and system integration 108 of aircraft 200 takes place. Thereafter, aircraft 200 may go through certification and delivery 110 in order to be placed in service 112. While in service by a customer, aircraft 200 is scheduled for routine maintenance and service 114 (which may also include modification, reconfiguration, refurbishment, and so on). While the embodiments described herein relate generally to servicing of commercial aircraft, they may be practiced at other stages of the aircraft manufacturing and service method 100. For example, a decontamination process may be implemented at various stages of aircraft production as many people have access to an aircraft and its components during a production process.

Each of the processes of aircraft manufacturing and service method 100 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 2, aircraft 200 produced by aircraft manufacturing and service method 100 may include airframe 202 with a plurality of systems 204 and interior 206. Examples of systems 204 include one or more of propulsion system 208, electrical system 210, hydraulic system 212, and environmental system 214. Any number of other systems may be included in this example. Although an aerospace example is shown, the principles of the disclosure may be applied to other industries, such as the automotive industry.

Apparatus and methods embodied herein may be employed during any one or more of the stages of aircraft manufacturing and service method 100. For example, without limitation, components or subassemblies corresponding to component and subassembly manufacturing 106 may be fabricated or manufactured in a manner similar to components or subassemblies produced while aircraft 200 is in service.

Also, one or more apparatus embodiments, method embodiments, or a combination thereof may be utilized during component and subassembly manufacturing 106 and system integration 108, for example, without limitation, by substantially expediting assembly of or reducing the cost of aircraft 200. Similarly, one or more of apparatus embodiments, method embodiments, or a combination thereof may be utilized while aircraft 200 is in service, for example, without limitation, to maintenance and service 114 may be used during system integration 108 and/or maintenance and service 114 to determine whether parts may be connected and/or mated to each other.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Figure 3:
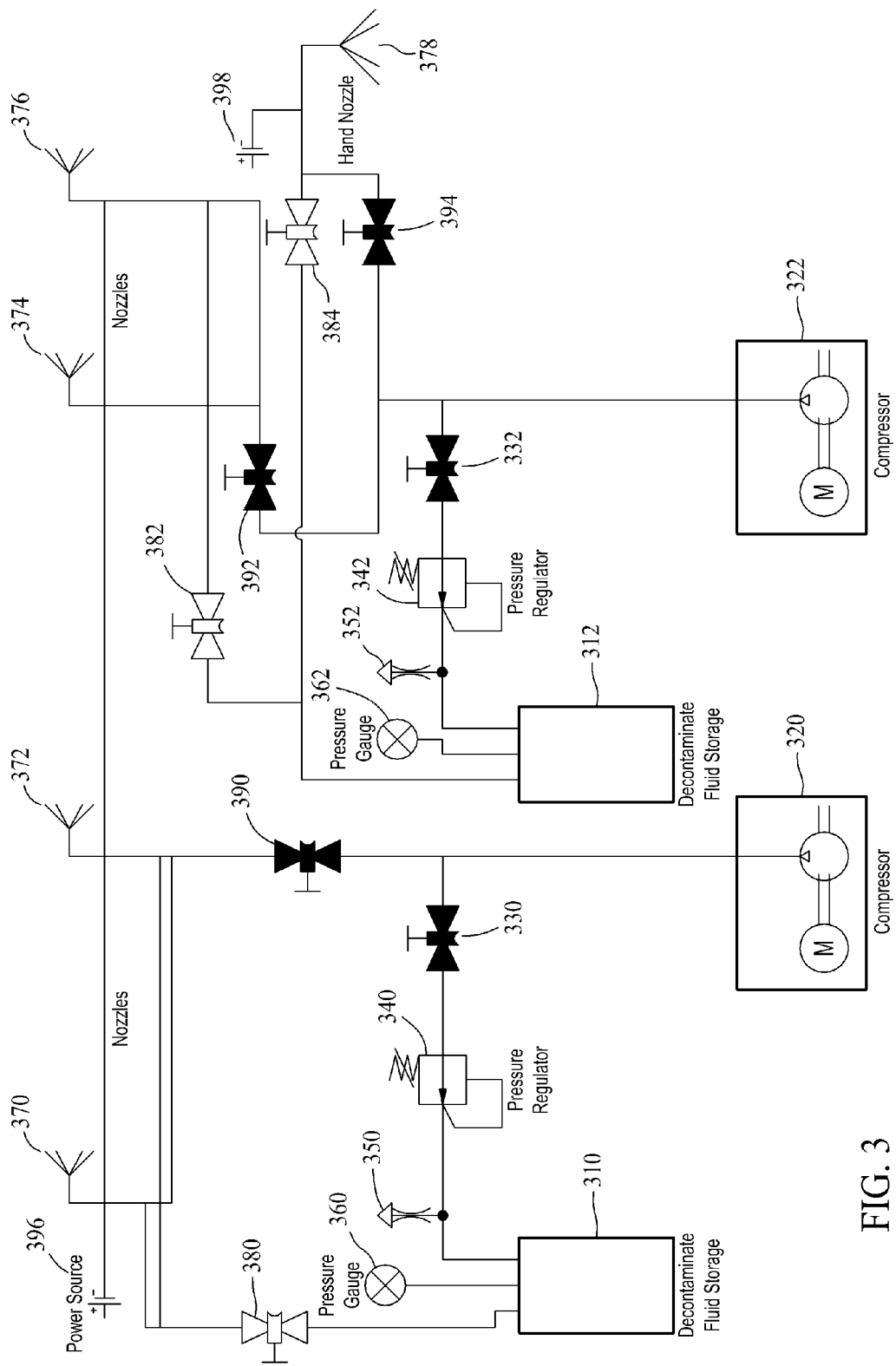
FIG. 3 is a schematic diagram of one embodiment of a decontamination system.

Turning now to FIG. 3, a schematic diagram of a decontamination product dispersion system 300 is depicted in accordance with an illustrative embodiment. System 300 includes two storage tanks 310 and 312, sometimes referred to as canisters, though it is easily understood that fewer or additional storage tanks could be incorporated into the system 300. The separate tanks 310 and 312 hold decontamination fluid, for example, of the type that cannot be stored together. Alternatively the tanks may hold the same fluid but be fluidly connected to different nozzles as described below. Each tank is fluidly coupled to a corresponding compressor 320 and 322 though is would be fairly straightforward to develop a system similar to system 300 that utilizes only one compressor.

Air from the respective compressors 320 and 322 passes through a compressed air shut off valve 330, 332, a pressure regulator 340, 342, and is operatively coupled to a pressure relief valve 350, 352 prior to entering the respective fluid storage tank 310, 312. Each of the tanks 310, 312 is in fluid communication with a pressure gauge 360, 362.

The embodiment of system 300 illustrated in FIG. 3 includes a plurality of nozzles 370, 372, 374, 376, and 378. In the embodiment, pressurized fluid from tank 310 passes through valve 380 (when opened) to nozzles 370 and 372. Prior to reaching nozzles 370 and 372, the pressurized fluid is combined with air pressure from compressor 320, which passes through valve 390 (when opened). Similarly, pressurized fluid from tank 312 passes through valve 382 (when opened) to nozzles 374 and 376. Prior to reaching nozzles 374 and 376, the pressurized fluid is combined with air pressure from compressor 322, which passes through valve 392. In the illustrated embodiment, nozzle 376 is a hand nozzle and is operated separately from nozzles 370, 372, 374, and 376. In the embodiment, pressurized fluid from tank 312 passes through valve 384 (when opened) to nozzle 378. Prior to reaching nozzle 378, the pressurized fluid is combined with air pressure from compressor 322, which passes through valve 394. In embodiments, nozzles 370, 372, 374, 376, and 378 are electrostatic nozzles. As such, power sources 396 and 398 are included within system 300, and provide power to the electrostatic charging system associates with the various individual nozzles.

Figure 4:
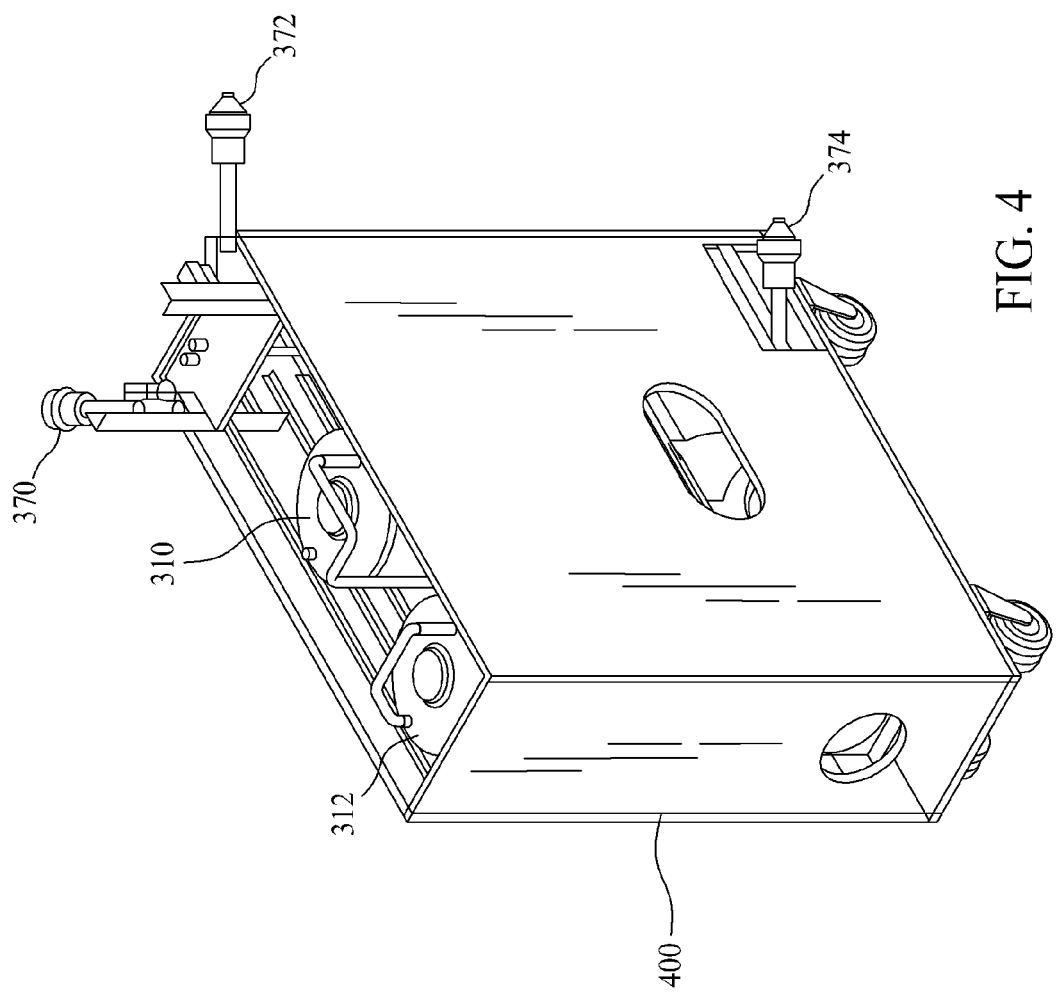
FIG. 4 is a perspective view of a cart in which the system of FIG. 3 may be deployed.

The above described system 300 is, in at least one embodiment, installed in a rolling cart 400 sized to fit in most vehicles such as aircraft and other transportation vehicles as depicted in FIG. 4. As further described, vaporous spraying nozzles, electrostatic charging of vapor droplets, and at least one air compressor are incorporated for vaporization and dispersion of decontamination fluid within vehicles such as ships, trains, and other large vehicles.

Referring specifically to FIG. 4, it is a perspective view of cart 400 which includes nozzles 370, 372, and 374 as well as tanks 310 and 312. This embodiment of cart 400 is sized for movement down the aisle of a typical commercial aircraft. Further, this embodiment of cart 400 is sized to be roughly the same dimensions as an aircraft galley cart, and can be stored within a commercial aircraft within one of the galley cart storage areas. In use, cart 400 can be pushed down the aisle of a commercial aircraft as maintenance personnel manually spray the seats and open overhead bins, lavatory doors and other compartments, with, for example nozzle 378 (shown in FIG. 3) which is denoted as being a hand operated nozzle (and shown in FIG. 5 in a storage location within cart 400). After the initial localized spraying, the cart 400 can be manually or automatically moved down the aircraft aisle while continuing to disinfect all the remaining surfaces in the vehicle, outputting the decontamination fluid droplets from the pre-positioned nozzles 370, 372, 374, and 376. In one embodiment, during the automatic operation of cart 400, an electrostatic dispersion spraying technique is performed by these nozzles to assure adherence of the decontaminating agent to the various surfaces of the aircraft for maximum effectiveness.

Figure 5:
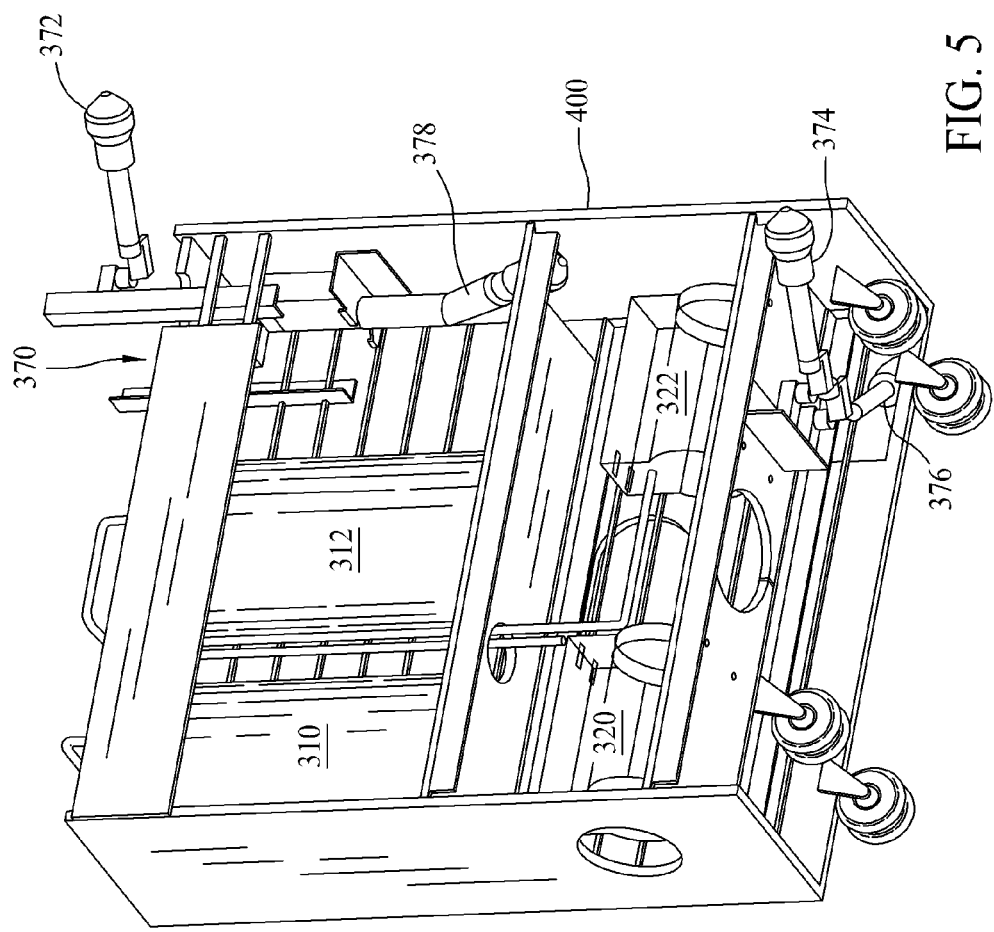
FIG. 5 is a side view of the cart of FIG. 4.

FIG. 5 is a side view of cart 400 with a cover panel removed. In this figure, one placement of tanks 310 and 312, air compressors 320 and 322 and nozzles 370, 372, 374, and 376 are shown as well as some of the fluid communication apparatus therebetween. In embodiments, nozzles 370, 372, 374, and 376 are stationary, with respect to cart 400, while in other embodiments nozzles 370, 372, 374, and 376 are capable of movement (automatic or manual) in one or more dimensions.

Figure 6:
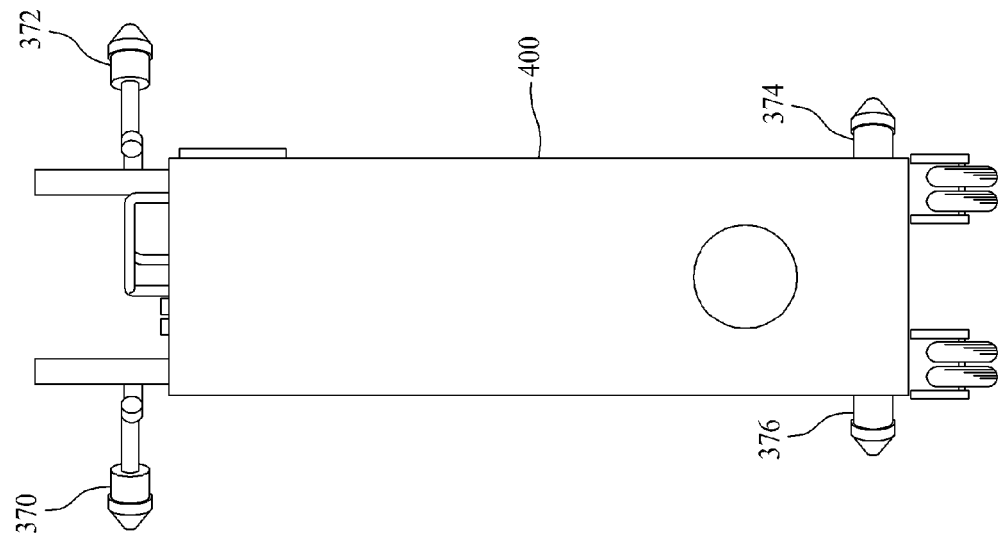
FIG. 6 is an end view of the cart of FIGS. 4 and 5.

An end view of cart 400, as shown in FIG. 6, provides further information regarding placement of nozzles 370, 372, 374, and 376 within cart 400 while also providing relative dimensions of cart 400. As can be easily discerned from review of FIG. 6, cart 400 is easily adaptable to provide decontamination capabilities for airlines. The service/food cart configuration of decontamination system 300 is easily available within an airplane in case of an outbreak of a germ or virus. Decontamination system 300 within cart 400 enables decontamination of an airplane and return of the aircraft to operation within a day. Droplets from decontamination system 300 are utilized to reach relatively complex geometric surfaces including the areas that are difficult for airline personnel to reach.

Figure 7:
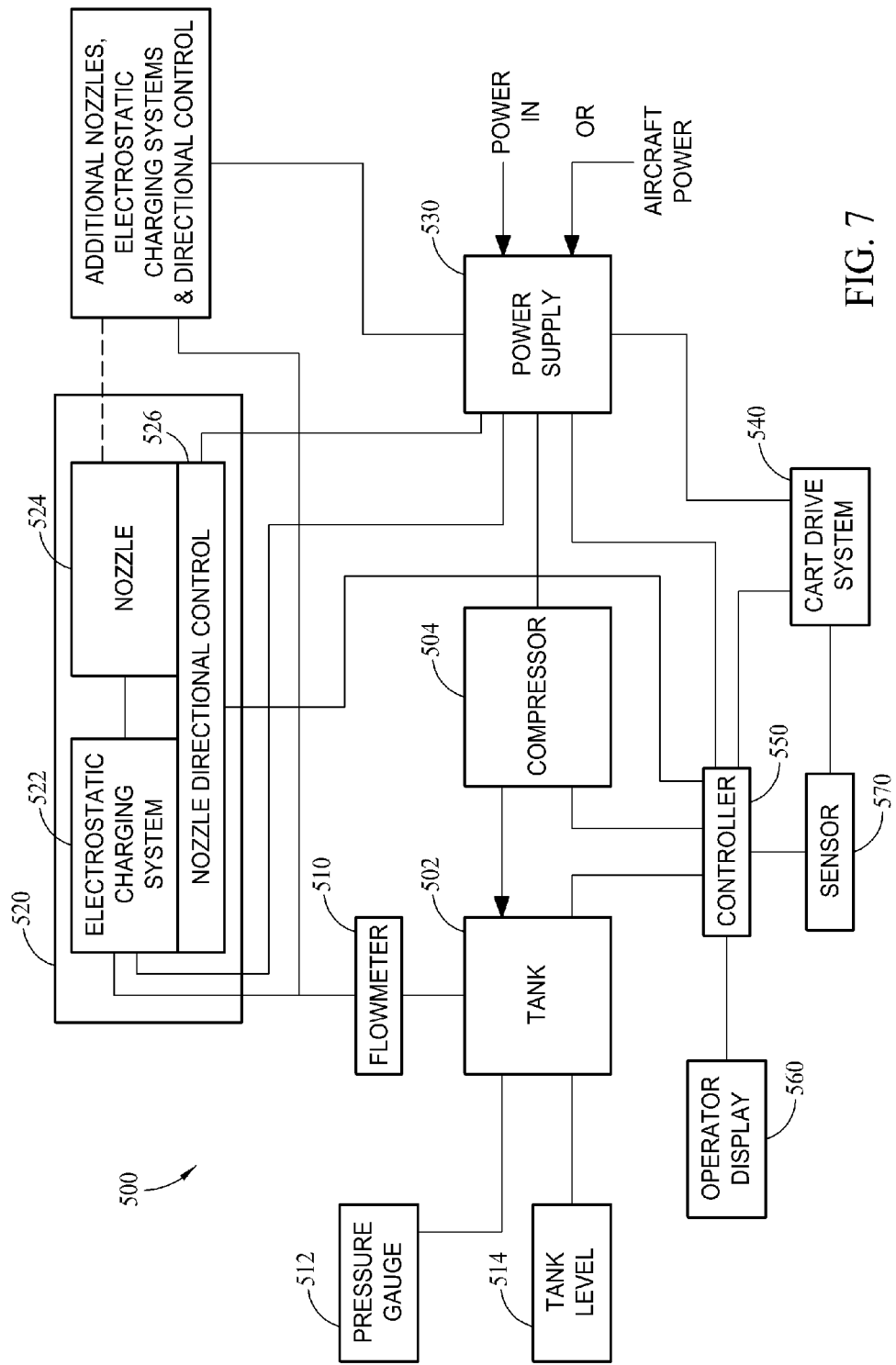
FIG. 7 is a block diagram of another embodiment of a decontamination system.

The above described cart 400 and system 300 may be modified to include many features and optional equipment. For example, FIG. 7 is a block diagram of a decontamination system 500, configured for placement on a cart, which illustrates several of these options. For simplicity, certain of the items described with respect to FIG. 1 are not shown or described with respect to FIG. 7.

In the illustrated embodiment, decontamination system 500 includes a tank 502 and compressor 504 which are fluidly connected to one another. Several items may be associated with tank 502 including a flowmeter 510 for measuring a flow of decontamination fluid out of tank 502, a pressure gauge 512 for measuring the pressure within tank 502, and a fluid gauge 514 for determining an amount of decontamination fluid remaining within tank 502.

As the pressurized decontamination fluid exits tank 502 and passes through flowmeter 510, it is dispersing to one or more nozzles. FIG. 7 illustrates the components of one nozzle system 520 that includes an electrostatic charging system 522, the nozzle 524, and a nozzle directional control 526. Note that one or more additional nozzle systems 520 may be incorporated into decontamination system 500. In embodiments, nozzle directional control 526 may include a stepper motor or other device that causes the nozzle 524 to move across a range of positions as the decontamination agent is dispersed.

A power supply 530 may be included within system 500 providing the voltage necessary to operate the compressor 504, the various electrostatic charging systems 522, the nozzle directional controllers 526, as well as a cart drive system 540 and a cart controller 550. In embodiments, power supply 530 utilizes an external power source, and in other embodiments, powers supply 530 utilizes aircraft generated power. The controller is utilized to control operation of the cart including movement of the cart via cart drive system 540, operation of the tank 502 and compressor 504 combination based on data received at a display 560. The controller 550 may be further programmed to provide signals to cart drive system 540 to control a rate of movement, and direction of movement of the cart. In embodiments, display 560 includes data from one or more of the flowmeter 510, pressure gauge 512, and tank level gauge 514.

For automatic movement of the cart using cart drive system 540, via controller 550, a sensor system 570 may be incorporated which in combination provides the function of maintaining the movement of the cart along a predefined course, for example, down the aisle of an aircraft, at a predefined rate.

The currently utilized decontamination methods include manual wipe out, use of manually operated spray distribution systems manually (e.g., a backpack type of system), or fogging of the vehicle. Manual wipe out, or spray distribution are very time consuming. A fogging method has to saturate the entire area. In the fogging operation, the sub-micron fog particles (less than 2 micron size of droplets) may stay suspended within an aircraft cabin, for example, for many hours. In addition, the fog particles may penetrate areas where such moisture is undesired, for example, wire bundles and sensitive avionics equipment, as well as leaving a residue in these areas. In contrast, cart 400 with system 300 installed therein allows the manual spraying of certain areas with minimal decontamination agent use and the automatic electrostatic vapor spray to disperse decontaminants that address the remaining areas using a single, simple to use system. The electrostatic aspect of the spray nozzles results in the dispersion of the charged decontamination agent which causes the particles to adhere to the various surfaces, for example, within the aircraft thereby also reduced the amount of time the particles are suspended in the compartment.

One unique aspect of system 300 is that it provides an easily adaptable, transportable, and effective decontamination tool for use within an aircraft interior and it is believed that decontamination times for a commercial aircraft will be reduced from days to hours with a far superior decontamination result. As illustrated by cart 400, system 300 can be easily stored onboard an aircraft and drastically reduce aircraft decontamination turn around time, positively impacting aircraft operation and contributing to airline cost saving.

Outside of commercial aircraft use, system 300 can easily be adapted for placement on other cart configurations for use in homeland security, private and military aircraft, permanent facilities (e.g., buildings), marine vessels, trucks, buses, trains and most any form of transportation, again providing reductions in vehicle and facility down time, cost savings, all in a stand alone system.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for dispersing a decontamination agent within a vehicle cabin, said method comprising:

dispersing the decontamination agent from a tank positioned within a rolling cart to one or more defined areas within the vehicle cabin;

positioning a plurality of automatically operated electrostatic nozzles at different heights along the rolling cart, the plurality of automatically operated electrostatic nozzles for distribution of the decontamination agent in at least one predetermined direction, wherein each automatic electrostatic nozzle is configured cycle through a predetermined range of motion for movement in one or more dimensions independently from each other when dispersing the decontamination agent, wherein the plurality of automatically operated electrostatic nozzles are selectively positioned between a spray position and a stowable position within the rolling cart, the plurality of automatically operated electrostatic nozzles remaining attached to the rolling cart when moved in the one or more dimensions;

applying an electrostatic charge to the decontamination agent with an electrostatic charging system connected to at least one of the plurality of automatically operated electrostatic nozzles, wherein the electrostatic charge is applied as the decontamination agent is dispersed; and pressurizing the decontamination agent with at least one compressor in communication with the tank, the at least one compressor capable of providing a pressure sufficient to provide a substantially constant distribution of the decontamination agent through at least one of the plurality of automatically operated electrostatic nozzles.

2. The method according to claim 1 further comprising moving the rolling cart along a defined path within the vehicle cabin.

3. The method according to claim 2 further comprising dispersing the decontamination agent from the tank to additional areas of the vehicle cabin via the plurality of automatically operated electrostatic nozzles, the dispersing occurring, at least in part, as the rolling cart moves along the defined path within the vehicle cabin.

4. The method according to claim 2 wherein moving the rolling cart along a defined path within the vehicle comprises operating a drive system connected to the rolling cart configured to impart a rate of motion upon the rolling cart.

5. The method according to claim 4 further comprising controlling the rate of motion of the rolling cart with the drive system.

6. The method according to claim 4 further comprising utilizing signals received from a sensor system to guide the rolling cart along the defined path.

7. The method according to claim 1 further comprising regulating a pressure within the tank generated by the at least one compressor.

8. The method according to claim 1 further comprising utilizing vehicle generated power to operate at least one of the electrostatic charging system or the at least one compressor.

9. The method according to claim 1 further comprising sizing the rolling cart to be received within a storage area operable for storing a cart.

* * * * *